US012649032B2

(12) United States Patent
Vamja

(10) Patent No.: US 12,649,032 B2
(45) Date of Patent: Jun. 9, 2026

(54) SYSTEMS AND METHODS FOR GUIDING A USER IN ADMINISTRATION OF A FLUID TO A SUBJECT

(71) Applicant: Joyce Vamja, Columbia, MD (US)

(72) Inventor: Joyce Vamja, Columbia, MD (US)

( * ) Notice: Subject to any disclaimer, the term of this patent is extended or adjusted under 35 U.S.C. 154(b) by 798 days.

(21) Appl. No.: 18/057,197

(22) Filed: Nov. 18, 2022

(65) Prior Publication Data

US 2023/0158242 A1    May 25, 2023

Related U.S. Application Data

(60) Provisional application No. 63/281,590, filed on Nov. 19, 2021.

(51) Int. Cl.
*A61M 5/31* (2006.01)

(52) U.S. Cl.
CPC ..... *A61M 5/3129* (2013.01); *A61M 2205/582* (2013.01); *A61M 2205/584* (2013.01); *A61M 2205/6009* (2013.01)

(58) Field of Classification Search
CPC .. A61M 2205/6009; A61M 2205/6045; A61M 5/3129; A61M 2205/582; A61M 2205/583; A61M 2205/584; A61M 2205/60; A61M 2205/6081
See application file for complete search history.

(56) References Cited

U.S. PATENT DOCUMENTS

| | | | | | |
|---|---|---|---|---|---|
| 4,072,146 | A | * | 2/1978 | Howes | A61M 25/0111 |
| | | | | | 600/487 |
| 4,219,021 | A | * | 8/1980 | Fink | A61M 39/223 |
| | | | | | 137/556.6 |
| 4,654,026 | A | * | 3/1987 | Underwood | A61M 39/08 |
| | | | | | 604/173 |
| 5,207,643 | A | * | 5/1993 | Davis | A61M 39/223 |
| | | | | | 604/80 |
| 5,224,932 | A | * | 7/1993 | Lappas | A61M 39/08 |
| | | | | | 604/173 |
| 5,423,750 | A | * | 6/1995 | Spiller | A61M 5/1407 |
| | | | | | 604/173 |
| 5,947,937 | A | * | 9/1999 | Urrutia | A61J 1/10 |
| | | | | | 604/905 |
| 5,974,708 | A | | 11/1999 | Webb et al. | |

(Continued)

FOREIGN PATENT DOCUMENTS

WO      WO-2017193082 A1 * 11/2017   .............. A61M 5/14

OTHER PUBLICATIONS

International Search Report and Written Opinion received in PCT/US22/80195, mailed on Feb. 21, 2023 (8 pages).

*Primary Examiner* — Cris L. Rodriguez

(74) *Attorney, Agent, or Firm* — Eleanor Musick; Torrey Pines Law Group PC

(57) ABSTRACT

A system and method for guiding a user in administration of a fluid to a subject are described herein. The fluid, which may contain medication, is introduced to the subject by an elongated tube with visual, tactile, or both visual and tactile indicators disposed near the distal and/or proximal ends of the elongated tube, the indicators meant to ensure the correct fluid enters the correct elongated tube and is delivered to the subject. A reference chart with tubing information and tubing accessories may also be used to further ensure that the correct fluid enters the correct elongated tube.

12 Claims, 13 Drawing Sheets

(56) References Cited

U.S. PATENT DOCUMENTS

Figure 1:
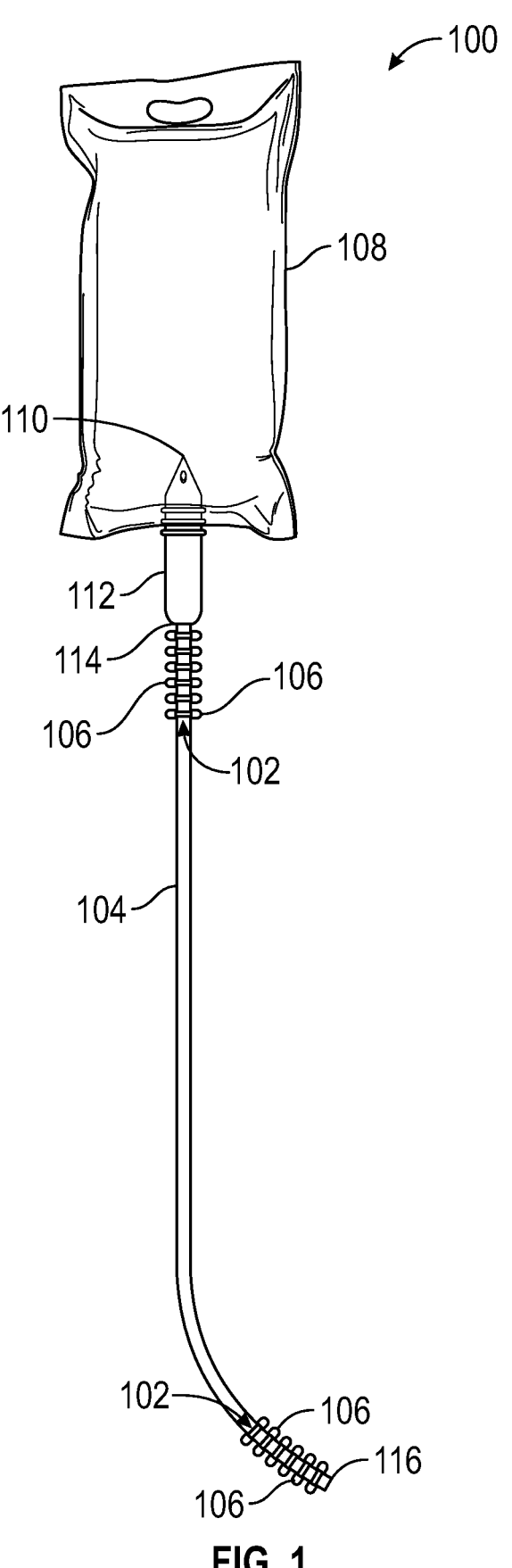

| | | | | |
|---|---|---|---|---|
| 6,823,617 | B2 * | 11/2004 | Schweikert | A61M 39/284 |
| | | | | 40/299.01 |
| 6,966,581 | B2 * | 11/2005 | Mastropaolo | F16L 35/00 |
| | | | | 285/422 |
| 7,338,476 | B2 * | 3/2008 | Kraushaar | A61M 5/14 |
| | | | | 604/523 |
| D573,255 | S * | 7/2008 | Stephens | D24/128 |
| 7,455,662 | B2 * | 11/2008 | Kraushaar | A61M 5/14 |
| | | | | 604/80 |
| 7,856,745 | B2 * | 12/2010 | Schweikert | G09F 3/205 |
| | | | | 40/658 |
| 8,430,865 | B2 * | 4/2013 | Lair | A61J 15/0003 |
| | | | | 604/910 |
| 9,205,024 | B1 * | 12/2015 | Mogaka | A61J 1/10 |
| 9,228,680 | B2 * | 1/2016 | Campbell | F16L 55/00 |
| 9,833,560 | B2 * | 12/2017 | Reichert | A61M 5/16813 |
| 10,157,266 | B2 * | 12/2018 | Dudar | G16H 20/17 |
| 10,357,643 | B2 * | 7/2019 | Buchanan | A61M 39/105 |
| 10,465,823 | B2 * | 11/2019 | Finnell | B65C 3/02 |
| 10,788,154 | B2 * | 9/2020 | Dudar | G16H 20/17 |
| 11,027,057 | B2 * | 6/2021 | Bone | A61M 5/1418 |
| 11,077,292 | B2 * | 8/2021 | Friedman | A61M 39/08 |
| 2005/0113798 | A1 * | 5/2005 | Slater | A61M 25/10 |
| | | | | 606/213 |
| 2005/0171492 | A1 | 8/2005 | Rodriquez | |
| 2005/0267404 | A1 * | 12/2005 | Kraushaar | A61M 5/14 |
| | | | | 604/80 |

| | | | | |
|---|---|---|---|---|
| 2006/0047251 | A1 | 3/2006 | Smith et al. | |
| 2007/0088286 | A1 * | 4/2007 | Brier | A61M 5/1408 |
| | | | | 604/189 |
| 2008/0097389 | A1 * | 4/2008 | Wilson | A61M 5/1408 |
| | | | | 604/82 |
| 2008/0097406 | A1 * | 4/2008 | Freed | A61M 5/1407 |
| | | | | 604/533 |
| 2008/0103486 | A1 * | 5/2008 | Owens | A61M 39/1011 |
| | | | | 604/533 |
| 2008/0243089 | A1 * | 10/2008 | Keaton | F16L 55/10 |
| | | | | 604/250 |
| 2012/0330238 | A1 * | 12/2012 | Robert | A61M 5/168 |
| | | | | 604/257 |
| 2013/0123743 | A1 * | 5/2013 | Adams | A61M 5/16831 |
| | | | | 604/151 |
| 2014/0031755 | A1 * | 1/2014 | Williams | A61M 39/1011 |
| | | | | 604/175 |
| 2015/0040987 | A1 | 2/2015 | Reichert et al. | |
| 2015/0196714 | A1 * | 7/2015 | Creaturo | A61M 5/31526 |
| | | | | 604/218 |
| 2016/0199569 | A1 * | 7/2016 | Yevmenenko | A61M 5/162 |
| | | | | 604/533 |
| 2018/0021512 | A1 * | 1/2018 | Fukuoka | A61M 5/165 |
| | | | | 604/404 |
| 2021/0121638 | A1 * | 4/2021 | Hernandez | A61M 5/31511 |
| 2023/0119157 | A1 * | 4/2023 | McGill | A61M 1/1565 |
| | | | | 604/29 |
| 2024/0066229 | A1 * | 2/2024 | Hernandez | A61M 5/3129 |

* cited by examiner

900

902 — Provide a system

904 — Introduce fluid to a container

906 — Observe the tubing stripe and feel the tactile elements

908 — Observe the roller or side clamp

910 — Check the chart

912 — Connect the tube

914 — Introduce fluid to the tube

916 — Administer the fluid

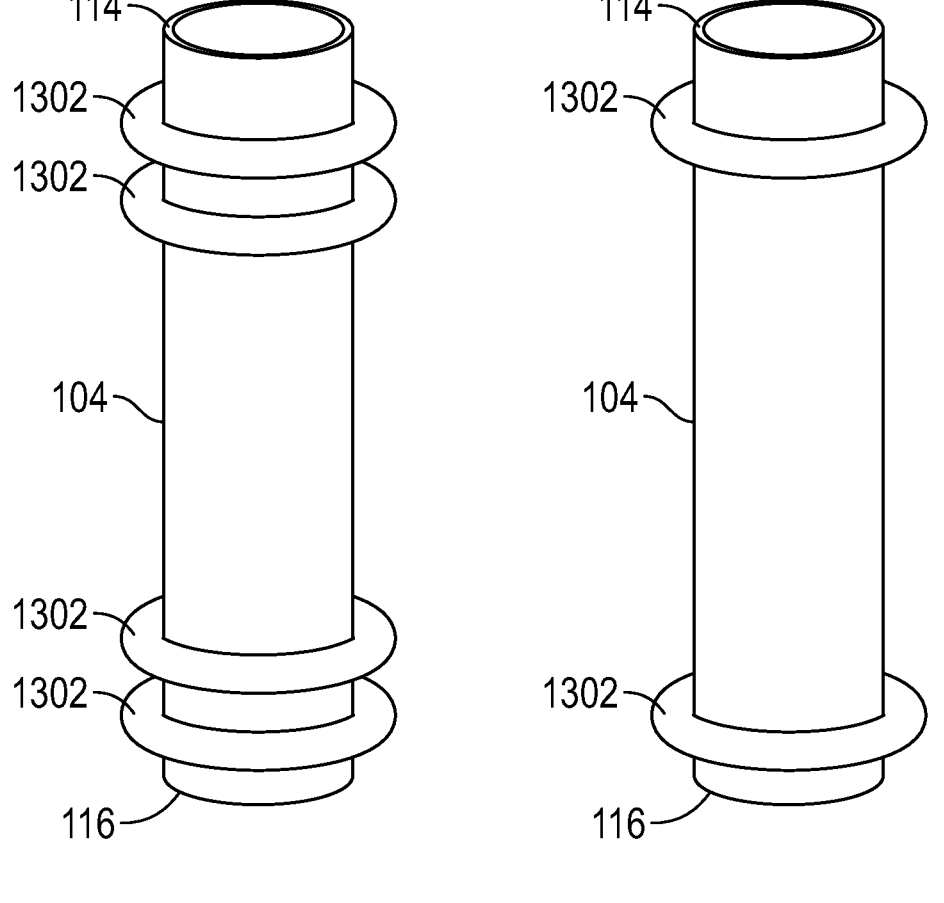
FIG. 13A          FIG. 13B

SYSTEMS AND METHODS FOR GUIDING A USER IN ADMINISTRATION OF A FLUID TO A SUBJECT

RELATED APPLICATIONS

This application claims the benefit of the priority of U.S. Application No. 63/281,590, filed Nov. 19, 2021, which is incorporated herein by reference in its entirety.

FIELD

The present teachings relate to systems and methods for guiding a user in administration of a fluid to a subject.

BACKGROUND

If a healthcare professional needs to administer fluid to a patient, it is important to ensure that the correct fluid is administered. What can oftentimes occur, especially if there are multiple healthcare professionals interacting with the subject, is fluid administration error.

Because of errors, users of the system are required to visibly confirm that the right fluid is going to the right access site on the subject. It is not uncommon for lines to be accidentally clamped, fluids being delivered at incorrect doses, or fluids going to the wrong access point. For instance, some fluids are very strong and cannot go into a peripheral IV; other fluids should never be introduced into an artery.

Throughout the entire process of a subject being under medical care, there are multiple interruptions that delay the timing of administering the correct fluid. Developing a system to deliver the correct fluid, minimizing fluid administration error, is of great importance.

A number of attempts have been made to address the issue of reducing medication administration errors. In one example, U.S. Pat. No. 6,059,768 of Friedman describes coded tubing for use with intravenous delivery that has a protruding ridge or depression, or an embedded visual indicator, which traverses a length of the tubing. Having either a ridge or a depression (a tactile indicator), or a visual indicator, which traverses the entire length of the tubing's surface may not provide the level of detail required to ensure that the correct tubing is being used for a specific, specialized connection downstream or upstream from the point at which the user inspects the tubing. As a result, the user may still be required to inspect the full length of tubing to confirm that the correct connections have been used, requiring additional time and attention.

U.S. Pat. Publ. No. 2002058928 2002/0058928 A1 of Antonio II describes an intravenous tube coding system that comprises colored bands that extend longitudinally along the full length of the tube. Similar to U.S. Pat. No. 6,059,768 of Friedman, longitudinal stripes (a visual indicator) may make it difficult to ensure that the correct tubing is used.

A similar approach to identification of medication syringes is disclosed in U.S. Pat. Publ. No. 2015/0238697 of Michaud et al. Tactile and visual differentiation features are located on the syringe tubes to distinguish between their contents. In most instances, the full length of the syringe includes the indicator which may be appropriate for the short length of a typical syringe but does not solve the issue of elongated tubing that may have multiple connectors along its length, and where each connection potentially has special requirements.

A solution that forces the user to focus on a particular area of the tube, such as the tube ends, to ensure correct tube usage can provide a standard that reduces the risk of fluid administration error. The risk of error will be further reduced if the tubing identification solution ensures correct fluid-tube combinations. It would be particularly desirable to incorporate multiple identification safeguards into a tubing system to ensure the correct fluid is connected to the correct tube. The need remains for such a standardized approach that is versatile enough to accommodate a wide array of fluid-tube combinations while making it even easier for users to quickly identify the correct tube to use, especially in dimly lit environments and instances in which there are multiple users handling the tubing.

SUMMARY

The coding system for guiding a user in administration of a fluid to a subject comprises an elongated tube formed from a tubing material, at least one annular feature disposed near at either the distal or proximal end of the elongated tube (or at both ends of the elongated tube), a reference chart that identifies to the user the annular feature associated with a fluid source, a connector, and a tubing accessory. The tubing accessory may comprise a number of components, such as roller clamps, side clamps, slide clamps, fittings, etc. The annular feature offers visual, tactile, or both visual and tactile indicators to ensure the intended fluid is delivered to the intended elongated tube. The reference chart and tubing accessory offer additional assurances that the intended fluid is delivered to the intended elongated tube. The fluid is documented on the reference chart. A user looks at the end of the elongated tube with the annular feature to check that the intended elongated tube is being used. There may be a single tubing accessory or multiple tubing accessories. Regardless of the number of tubing accessories, they may be part of a process to ensure intended fluid-tube combination. The annular feature at the distal and proximal ends of the elongated tube encircles the elongated tube circumferentially, not axially across the length of the elongated tube. A user must look at the ends of elongated tube, a practice that can be standardized to ensure the intended elongated tube is used for the intended fluid. In addition, the number of annular features at the distal end of the elongated tube matches the number of annular features at the proximal end of the elongated tube. The colors of the annular features are pronounced and easily visible, even in dimly lit environments. A reference chart that identifies tubing information may be used for fluid identification purposes and be part of a standardized process for making sure that the intended fluid goes to the intended elongated tube. Such a process may involve a user looking at the annular feature, looking at the tubing accessory, and looking at the reference chart to ensure appropriate fluid-tube combination. It is not necessary for these steps to be followed in this specific order, though. These measures, used in a consistent manner, provide an ideal way to check intended fluid-tube combination. As an example, a user may check the annular feature and tubing accessory, and add the fluid to the elongated tube. Before administering the fluid to a subject, the user may check off on the reference chart that that specific fluid is to be administered by locating the correct annular feature number configuration on the reference chart. For instance, if fluid X is to be administered, and fluid X corresponds with 1 annular feature, fluid X may be checked off on the reference chart at the section on the chart that denotes 1 annular feature. At an end of the elongated tube, the annular features may be monochrome or have multiple colors. In either case, such a standard denotes a different type of fluid to be administered to a subject. For instance, all black annular features signify a certain fluid. In another configuration, a mix of black and red annular features signify another fluid. The color of the annular features matches at the distal end and the proximal end of the elongated tube (e.g. if there are all black annular features at the distal end of the elongated tube, there are all black annular features at the proximal end of the elongated tube). The tubing accessories are used for pinching off the elongated tube to expel bubbles from the elongated tube and to restrict fluid from moving past the tubing accessory, with the tubing accessory also acting as a check to ensure the intended fluid is in the intended elongated tube. The tubing accessory may act as such a check by it having indicators that match the annular features affixed to the elongated tube. The tubing accessory indicators may comprise a number of forms, such as stripes, bumps, dimples, or the like. For instance, if there are 3 annular features disposed near the end of an elongated tube, there may be 3 stripes affixed to the tubing accessory. The elongated tube may be made from a variety of materials, some of which are polyvinyl chloride, polyethylene, polyurethane, nylon, silicone, and thermoplastic elastomers. Having a visual indicator at the distal and/or proximal ends of the elongated tube allows for one to focus solely on one area of the elongated tube (an end) to ensure the intended fluid-tube combination will be made. Users train their eyes on the elongated tube ends as opposed to potentially looking at the entire tube to make sure that the intended elongated tube is in use. Such an approach makes it easy to develop protocols for checking fluid-tube combinations. Focusing on one area instead of potentially focusing on many areas lowers the likelihood of unintended fluid-tube combinations.

The annular feature may comprise one or more or a combination of tactile elements disposed near the proximal end of the elongated tube, the distal end of the elongated tube, or both the distal and proximal ends. Serving as part of the checking process to ensure intended fluid-tube combination, the tactile elements are in close proximity to visual indicators and may be positioned as a row of tactile elements for easy counting. In some embodiments, a tactile element is in physical contact with or physically touching the visual indicator. In other embodiments, a tactile element is adjacent to a visual indicator. The number of tactile elements is a multiple of the number of visual indicators. The multiple depends on the spacing of the tactile elements around the circumference of the elongated tube. For instance, if the visual indicators are stripes, and there are 5 stripes, there may be 5 tactile elements (a multiple of 1), 10 tactile elements (a multiple of 2), 15 tactile elements (multiple of 3), 20 tactile elements (multiple of 4), etc. As one looks at the distal and/or proximal end of the tube, there may be 1 row of 5 tactile elements, 2 rows of 5 tactile elements, 3 rows of 5 tactile elements, 4 rows of 5 tactile elements, and so on. The tactile elements may be implemented into a protocol for checking for intended fluid-tube combination by counting the tactile elements visually or physically touching them to count them. After counting or touching the number of tactile elements, a user can also refer to the reference chart to ensure that the intended fluid goes to the intended elongated tube. In an embodiment, the tactile elements may exist in a row on the outer surface of the tube, the row of tactile elements in close proximity with the visual indicators. In the same embodiment, other rows of tactile elements may be located circumferentially around the outer surface of the elongated tube, with all rows of tactile elements matching each other in number. For instance, if there are 5 tactile elements in one row, there may be another row of 5 tactile elements located circumferentially from the first row of tactile elements. Also, the number of tactile elements disposed near the distal end of the tube matches the number of tactile elements disposed near the proximal end of the elongated tube. The number of rows of tactile elements disposed near the distal end of the elongated tube matches the number of rows of tactile elements disposed near the proximal end of the elongated tube. Since the tactile elements are disposed near the elongated tube ends, it trains users to focus on the ends to count them visually or touch them which, similar to the visual indicators, helps in developing a standardized protocol for checking fluid-tube combinations (i.e. look at the ends), and it also helps to even further minimize fluid administration error. Looking at the visual indicators, the tactile elements, and tubing accessories, and comparing that information to that on the reference chart can be developed as a standardized protocol that users may repeatedly use to ensure intended fluid goes to the intended elongated tube.

The elongated tube may be at least one of gravity tubing, vented intravenous tubing, primary tubing, secondary tubing, and non-vented intravenous tubing, or other conventional tubing types that is well known in the art.

The tubing accessory may have at least one visual indicator. The visual indicator of the tubing accessory may be used to match it with the appropriate elongated tube and allow one to clamp shut the correct infusion. The visual indicator of the tubing accessory matches the annular feature disposed near the elongated tube ends. If the tubing accessory is a clamp and the visual indicators are stripes, looking at the stripe or stripes on the clamps may serve as part of the protocol to ensure intended fluid-tube combination.

The tactile elements are spaced well enough that they are easy to count or touch without making a counting error. They allow a user to quickly feel tubing and to make sure the intended fluid goes to the intended elongated tube (and the fluid is being administered to the intended subject). Particularly in poorly lit environments, where it may be difficult to see visual indicators, having tactile elements is an added measure to ensure that there is intended fluid-tube combination. Adjacent tactile elements may be spaced between 0.01 inches and 1 inch apart.

The present teachings include a method of guiding a user in administration of a fluid to a subject. Providing such a system is a step, the components of the system comprising an elongated tube, at least one annular feature disposed near one of the distal end and proximal end of the elongated tube, a reference chart that identifies the annular feature, and a tubing accessory that corresponds to the annular feature. Another step is to introduce the fluid to a container. The fluid is documented on the reference chart. A healthcare professional, possibly a nurse, then observes a visual indicator on the tubing accessory to ensure that the fluid corresponds to the annular feature. The healthcare professional may also check the reference chart to ensure that that color and number of annular features coincide with the information on the reference chart. The distal end of the elongated tube connects via a connector with a container holding a fluid and the proximal end of the elongated tube connects via a connector with a subject. The fluid is introduced from the container to the elongated tube via the elongated tube's distal end, followed by administering the fluid to the subject via the elongated tube's proximal end. Different fluids correspond to different number of annular features. Having a method that minimizes variability in administering the fluid makes it less likely that there are fluid administration errors. A method such as: Look at the annular features (which are disposed near the elongated tube ends), make sure the tubing accessories' visual indicators coincide with the annular features of the elongated tube, check the reference chart to make sure the annular features coincide with the information on the reference chart, allow the fluid to enter the elongated tube at its distal end, and administer the fluid to the subject via the elongated tube's proximal end can greatly decrease fluid administration errors.

According to an exemplary embodiment, a system for guiding a care provider in the administration of fluids to a subject includes an elongated tube having one or more unique indicators disposed at least one of a distal end and a proximal end of the tube at which a connection is to be made. The unique indicator may be distinguishable by a user through visual, tactile, or a combination of visual and tactile sensing. In some embodiments, the indicators may be one or more tubing stripes formed on a surface of the elongated tube or embedded in the elongated tube. The stripes may be a single color or a combination of colors. The stripes may have a smooth texture, e.g., imprinted on the tube, or a raised or lower surface relative to the outer surface of the tube, e.g., annular ribs or channels. Where multiple stripes are used, varied stripe thicknesses and/or spacings between the stripes may also define a unique identifier. The stripes may have a continuous surface or may be formed from a series of tactile features such as bumps, raised dots, grooves, or dimples. Combinations of the variety of stripe characteristics such as quantities, colors, widths, spacings, and surface textures act as a code that corresponds to a reference chart that is used to identify a type of connector, or type of fluid, with which the tube is to be used, and to which the elongated tube end with the stripes is to be connected.

In some embodiments, a tubing accessory, such as a roller or pinch clamp, may have a corresponding indicator formed thereon to allow the user to select the appropriate clamp for the fluid to be administered.

DRAWINGS

Those of skill in the art will understand that the drawings, described below, are for illustrative purposes only. The drawings are not intended to limit the scope of the present teachings in any way.

FIG. 1. Depiction of the system with a tube connected to an intravenous bag.

Figure 2:
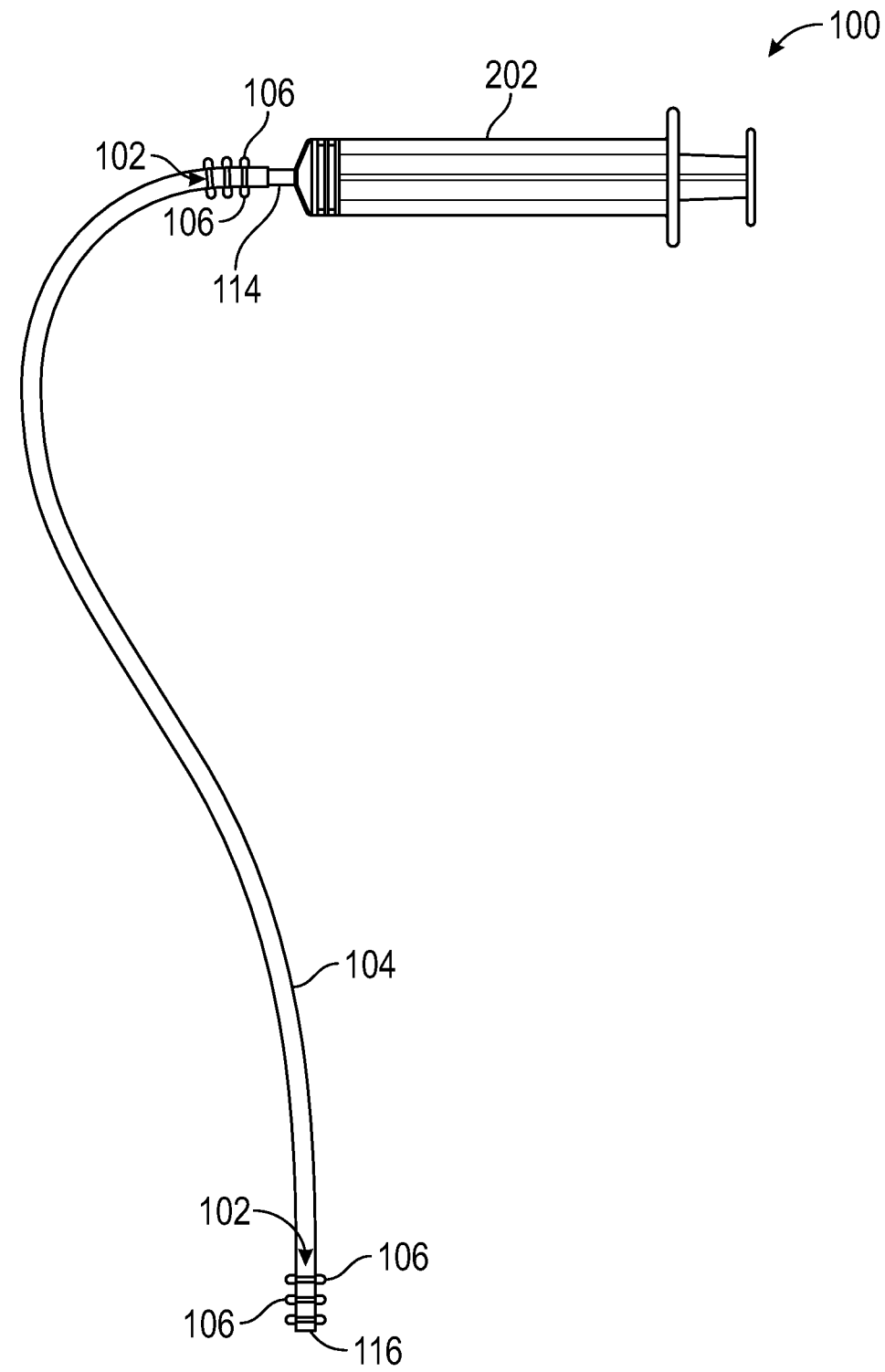

FIG. 2. Depictions of the system with a tube connected to a syringe.

Figure 3:
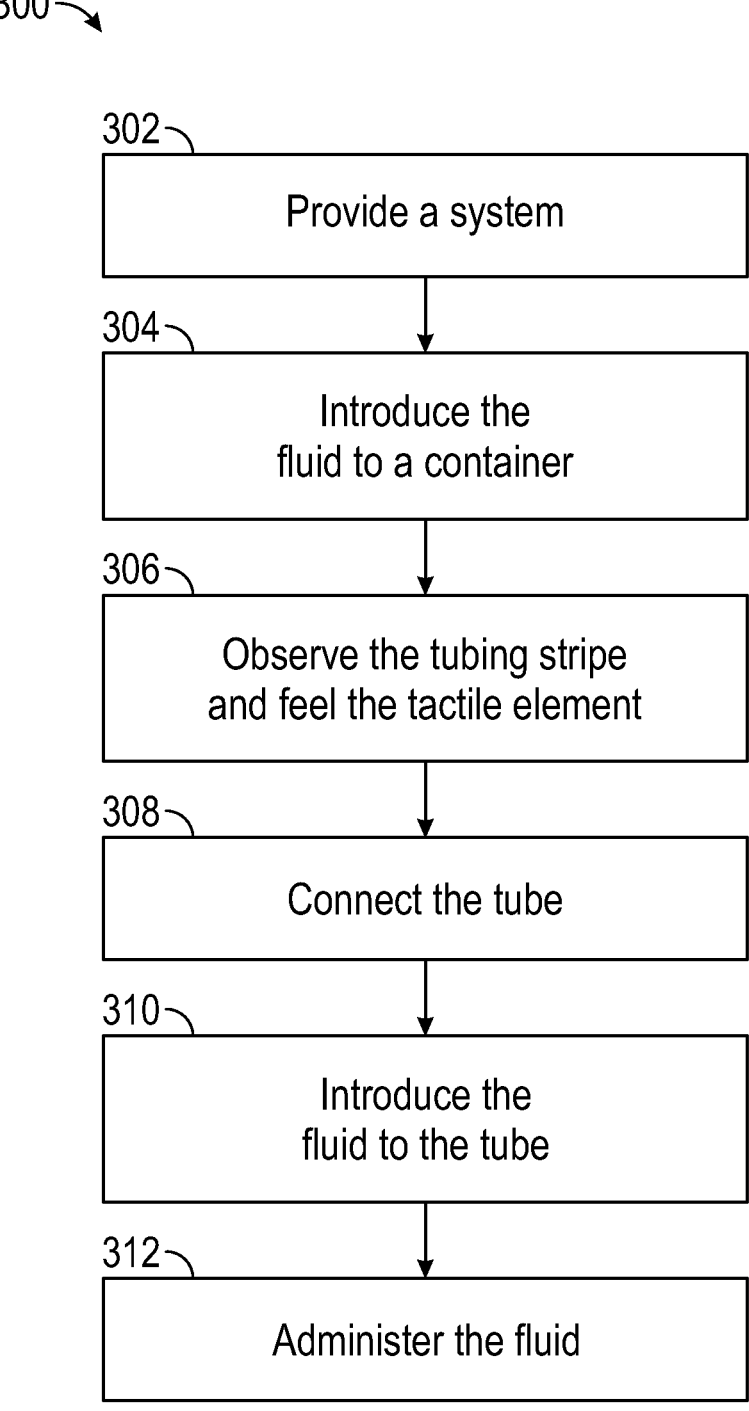

FIG. 3. A flowchart depicting a method of guiding a user in administration of a fluid to a subject.

Figure 4:
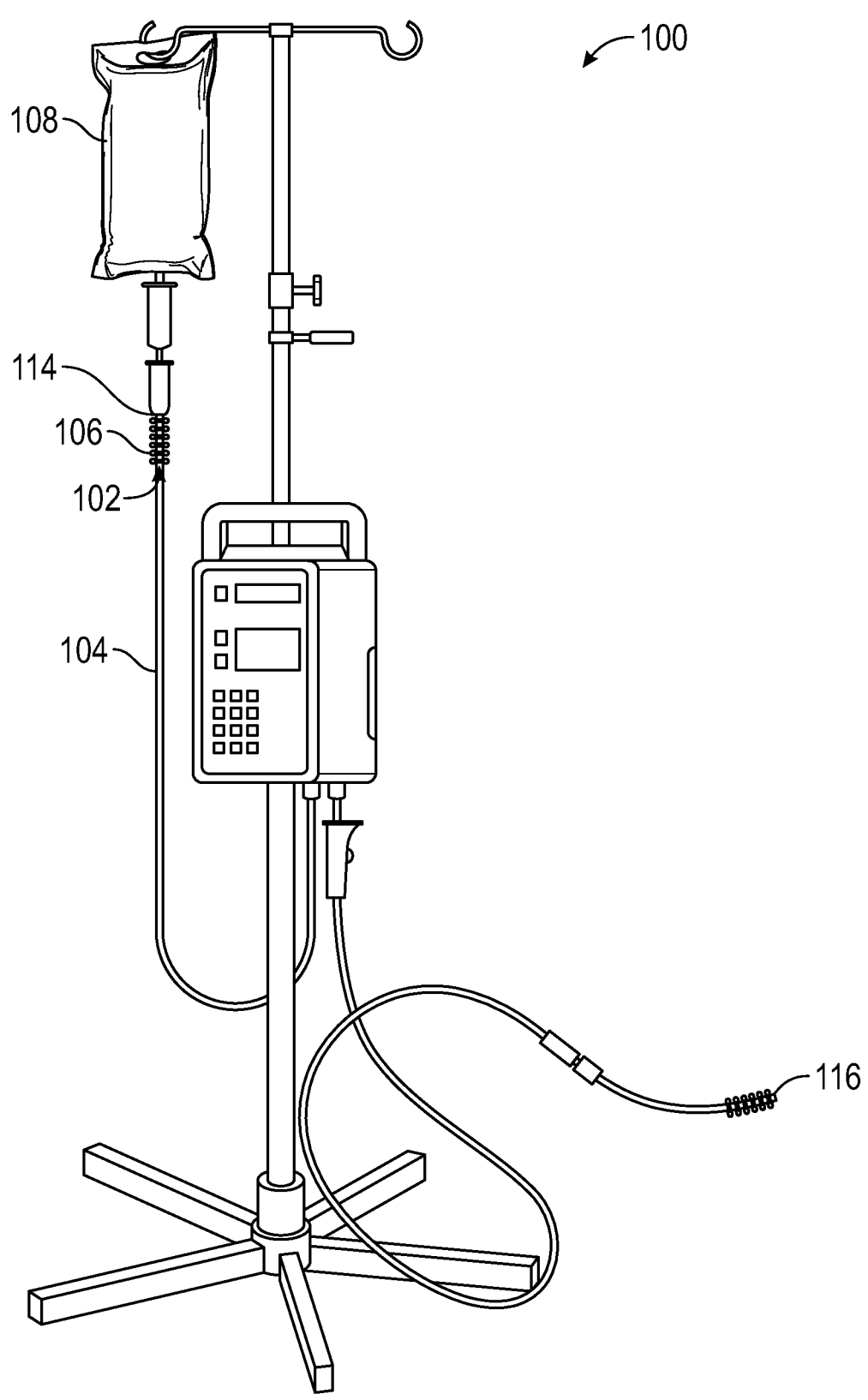

FIG. 4. Alternative depiction of the system, showing a tube connected to an intravenous bag.

Figure 5:
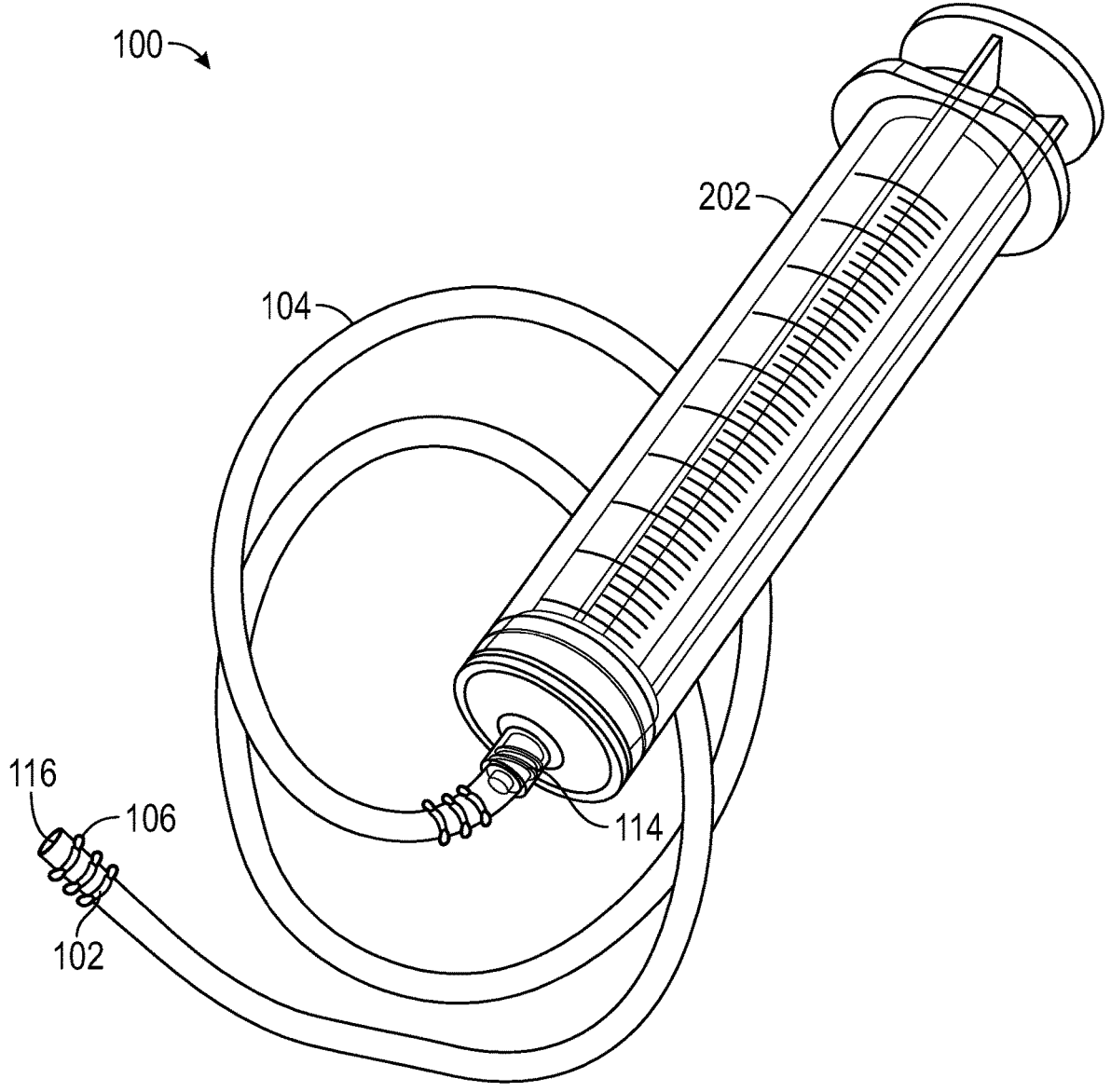

FIG. 5. Alternative depiction of the system, showing a tube connected to a syringe.

Figure 6A:
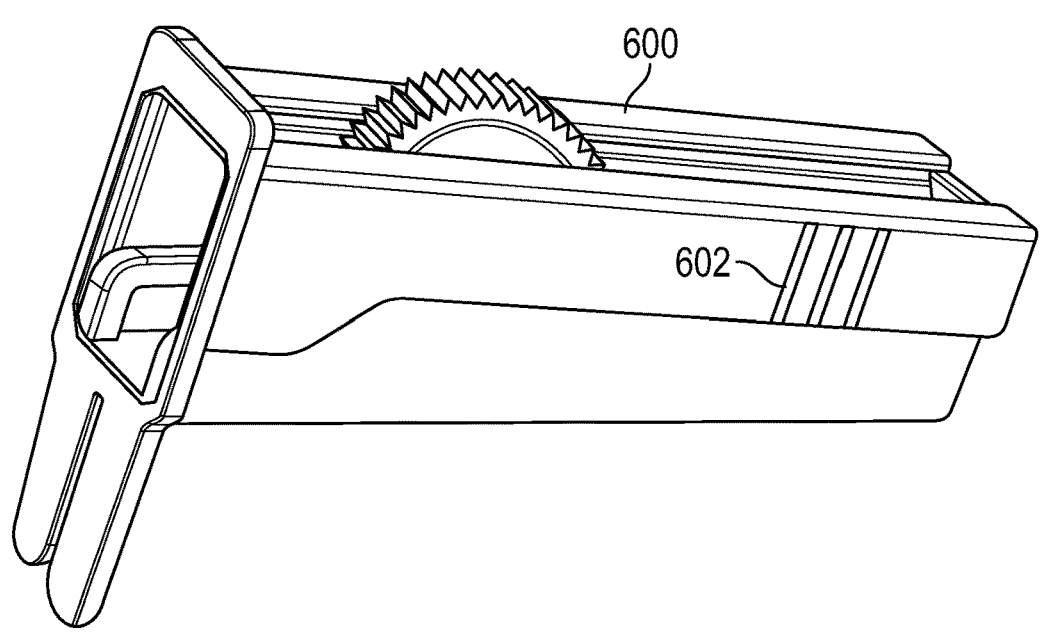
Figure 6B:
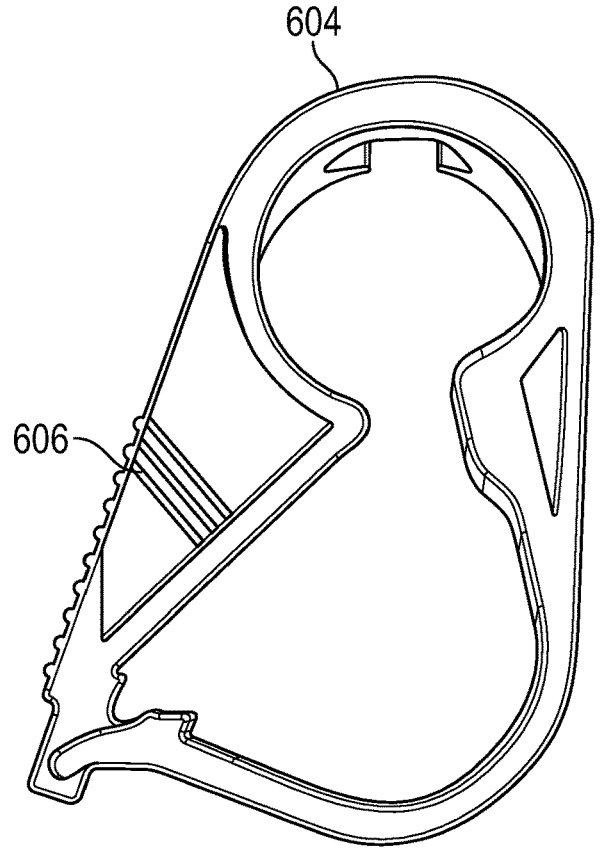

FIGS. 6A-B. Exemplary depictions of a roller clamp (FIG. 6A) and side claim (FIG. 6B)

Figure 7:
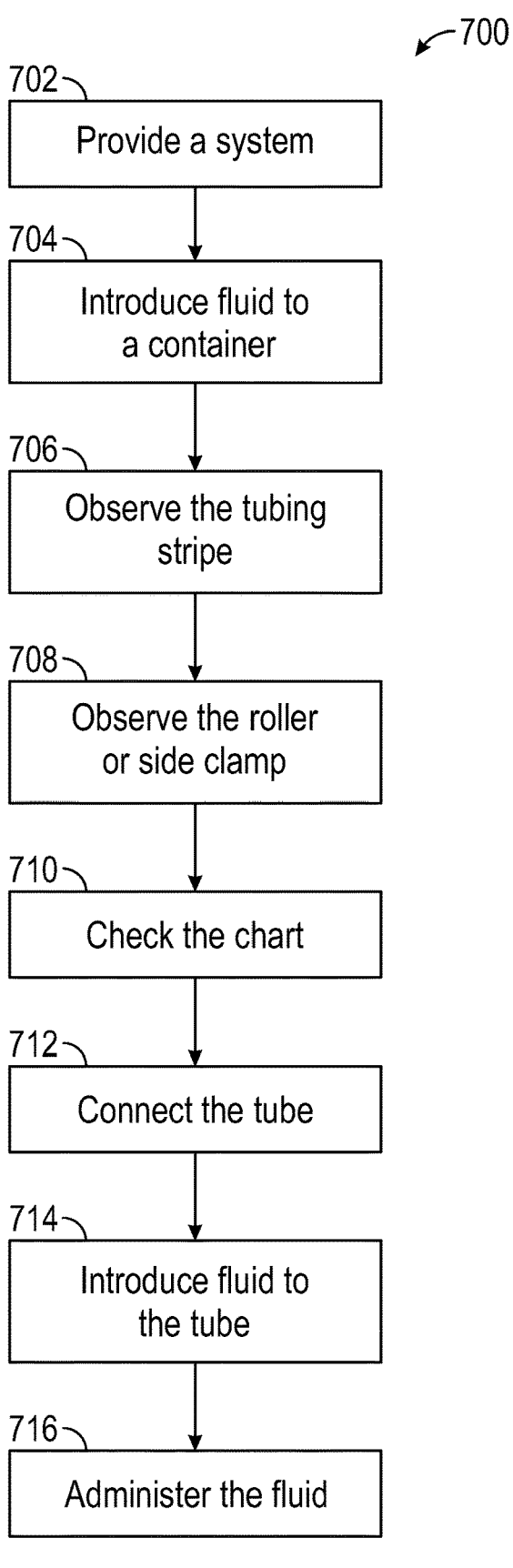

FIG. 7. A flowchart depicting another exemplary method of guiding a user in administration of a fluid to a subject.

Figure 8:
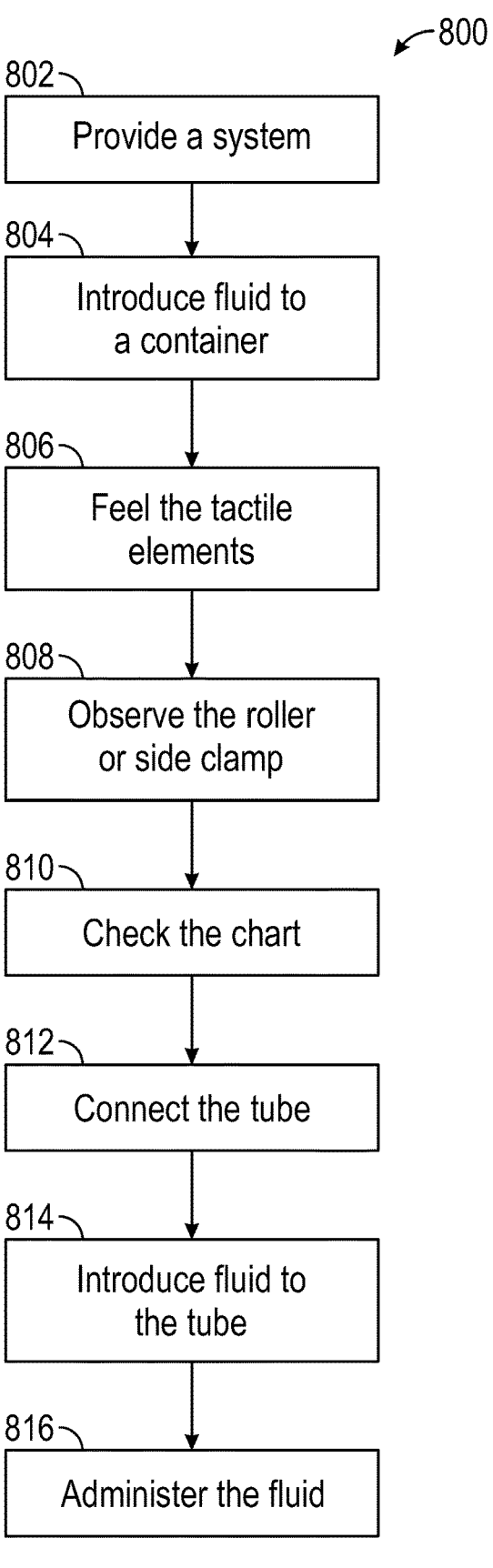

FIG. 8. A flowchart depicting yet another exemplary method of guiding a user in administration of a fluid to a subject.

Figure 9:
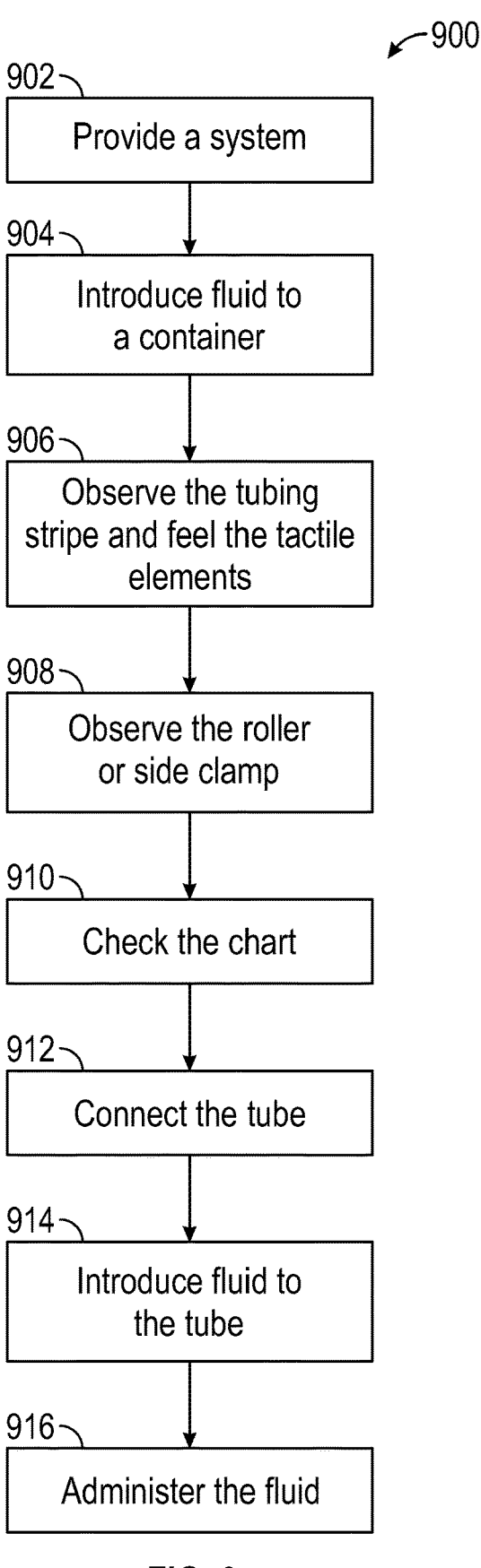

FIG. 9. A flowchart depicted yet another exemplary method of guiding a user in administration of a fluid to a subject.

Figure 10C:
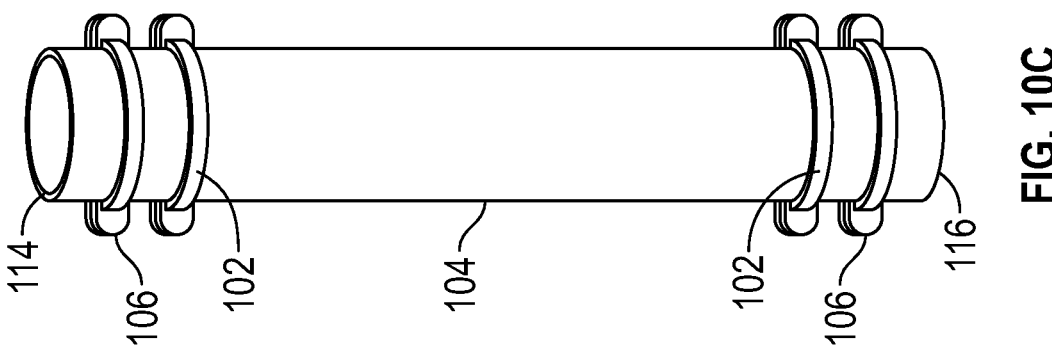
Figure 10B:
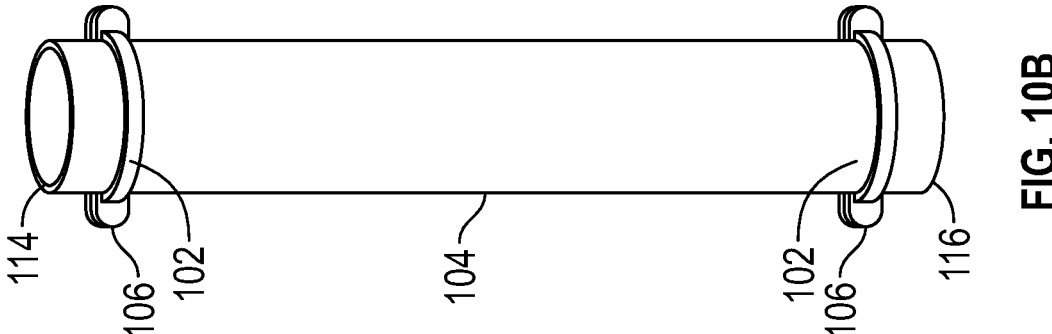
Figure 10A:
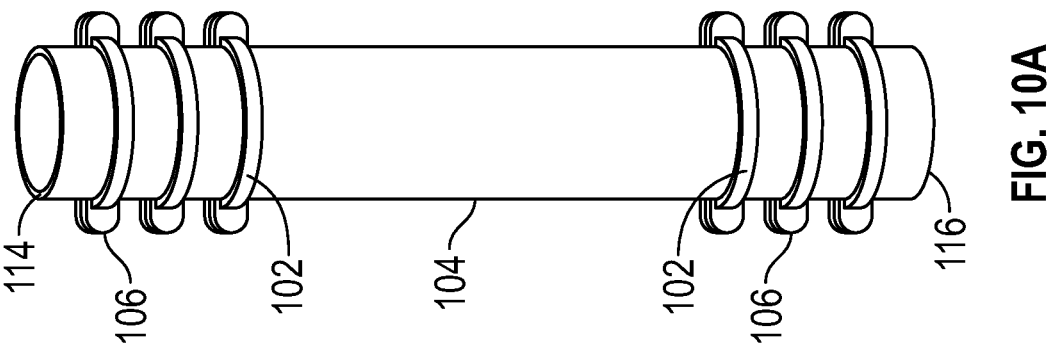

FIGS. 10A-C. Exemplary depictions of an elongated tube with various numbers of visual and tactile indicators.

Figure 11A:
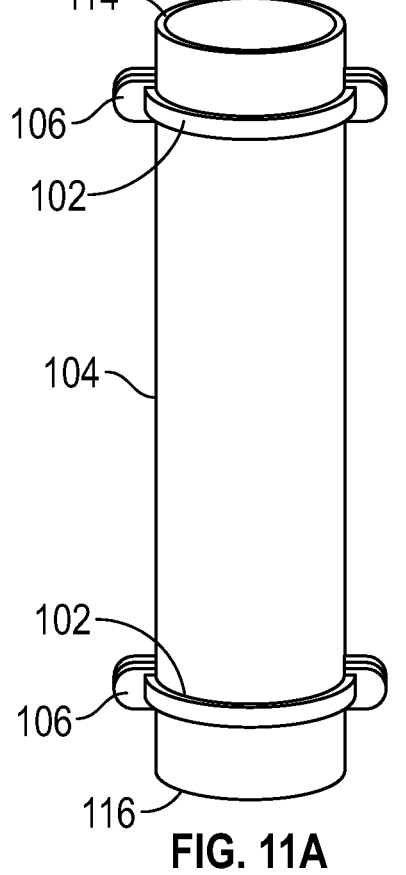
Figure 11B:
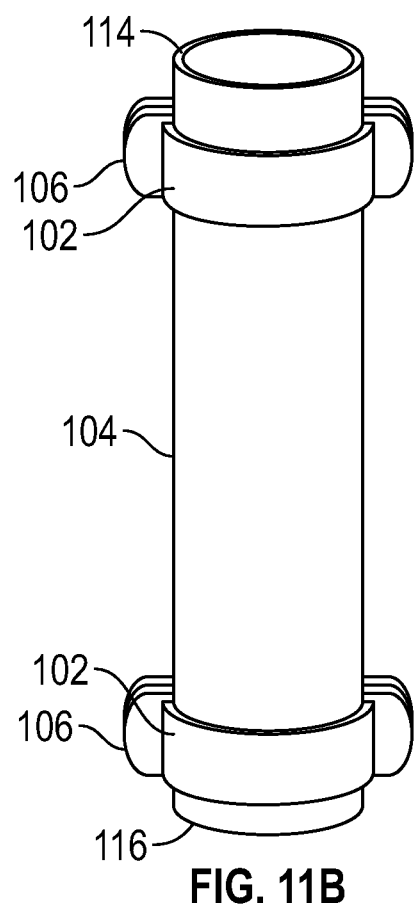

FIGS. 11A-B. Exemplary depictions of a tube with various sizes of visual and tactile indicators.

Figure 12A:
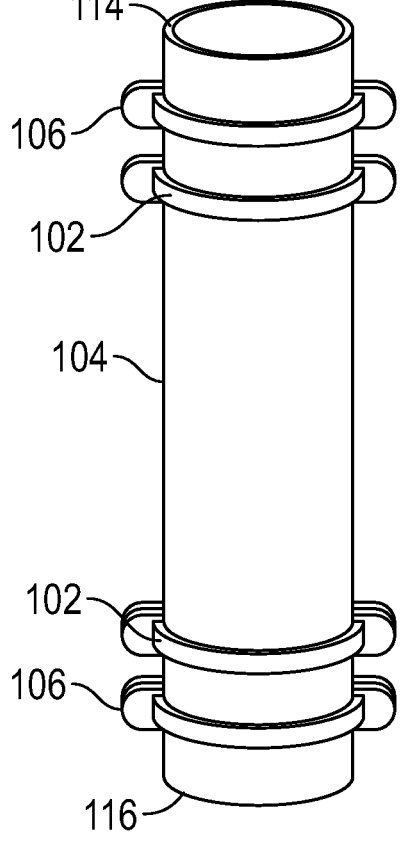
Figure 12B:
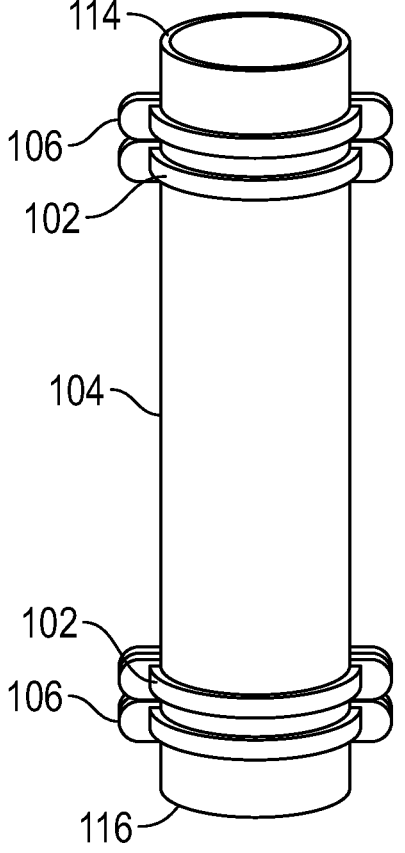

FIGS. 12A-B. Exemplary depictions of a tube with various spacing of visual and tactile indicators.

FIGS. 13A-B. Exemplary depictions of an elongated tube with a visual-tactile combination indicator.

DETAILED DESCRIPTION OF EMBODIMENTS

The present invention is directed to a coding system 100 that delivers fluid, typically in the form of a fluid, to a subject, such as a patient or other person to whom fluid administration is appropriate. In some applications, the fluid is an intravenous (IV) bag 108, as shown in FIG. 1. A spike 110 punctures the bag 108, allowing fluid to enter a drip chamber 112. Fluid from the drip chamber 112 may then enter a distal end 114 of the elongated tube 104. The fluid travels through the elongated tube 104 to reach a proximal end 116 of the elongated tube 104. The distal end 114 is the end furthest from the subject during the fluid administration process; the proximal end 116 is the end closest to the subject during the fluid administration process. The elongated tube 104 has at least one annular feature disposed near the distal end 114, the proximal end 116 or both the distal end 114 and the proximal end 116. The annular feature is visually distinguishable from the elongated tube 104, tactilely distinguishable from the elongated tube 104, or both visually and tactilely distinguishable from the elongated tube 104. In other words, the annular feature may comprise visual indicators/elements, tactile indicators/elements, or both visual indicators/elements and tactile indicators/elements. In some embodiments, visual indicators take the form of a stripe or a plurality of tubing stripes 102. The tubing stripes 102 may be imprinted on the elongated tube 104, with tubing stripes 102 separated by spacings. The tubing stripes 102 may comprise one or more visually distinguishable colors, hues, patterns, and spacings. The annular feature may comprises one or tactile elements 106, with the tactile 106 selected from raised annular ribs, an array of bumps, a ring of bumps, an annular groove, an array of dimples, and a ring of dimples. A plurality of tactile elements 106 may be separated by spacings. The tactile elements 106 may comprise one or more visually distinguishable colors, patterns, and spacings. The annular feature may also comprise a plurality of stripes 102 and tactile elements 106. The tubing stripes 102 and tactile elements 106 are located near the distal end 114 and the proximal end 116. In another embodiment, the tubing stripes 102 and tactile elements 106 are disposed near at the distal end 114. In another embodiment, the tubing stripes 102 and tactile elements 106 are disposed near at the proximal end 116. The number of tubing tactile elements 106 corresponds with the number of stripes 102 by a multiple. The multiple depends on the spacing of the row of tactile elements 106 around the surface of the tube 104. With larger spacing, the multiple is smaller than with smaller spacing. If there are 3 tubing stripes 102, there may be 2 rows of 3 tactile elements 106, 3 rows of 3 tactile elements 106 (not shown), 4 rows of 3 tactile elements 106 (not shown), and so on. In this instance, there may even be 1 row of 3 tactile elements 106 (not shown). Different tubing stripes 102, and corresponding number of tactile elements 106, indicate different fluids for administration to a subject. The tubing stripe 102 encircles the exterior surface of the elongated tube 104, the interior surface of the elongated tube 104 or both the exterior and interior surface of the elongated tube 104. As the annular features may comprise visual indicators, tactile indicators, or both. While FIG. 1 shows an exemplary embodiment of the invention, it is not meant to be limiting, as different visual and tactile indicators may be used, as long as they are disposed near the distal end 114 and/or proximal end 116 of the elongated tube 104.

FIG. 2 depicts the system 100 with the fluid container being a syringe 202. The distal end 114 of the tube 104 connects to the syringe 202. Fluid expressed from the syringe 202 moves through the distal end 114 and through the tube 104 to the proximal end 116, with the fluid ultimately administered to a subject.

FIG. 3 shows an exemplary method 300 for guiding a user in administration of a fluid to a subject. Providing the system 302, whether the fluid originates from an intravenous bag 108 or a syringe 202, is a step that ensures that the correct equipment is available. Another step is introducing the fluid to a container 304. A further step is observing the tubing stripes and feeling the number of tactile elements 306. Feeling the number of tactile elements is especially helpful in poorly lit environments. It is important to make sure that the fluid in the container is the intended one that should be introduced to the elongated tube. Viewing the tubing stripes and feeling the number of tactile elements assist in determining that the intended fluid enters the elongated tube. A further step is to connect the tube 308 to the ends of the tube via means known in the art. Introducing the fluid to the tube 310 is another step, from the distal end to the proximal end closest to the subject. Once the fluid exits the proximal end, it enters the subject 312 via a port or via an entry point. Based on the fluid, the subject may receive the fluid at various flowrates and within certain timeframes.

FIG. 4 is an alternative depiction of the system 100 with the tube 104 connected to an intravenous bag 108. The distal end 114 of the tube is further from the subject than the proximal end 116 of the tube, closer to the subject when the system 100 is connected to the subject. The tubing stripes 102 and tactile elements 106 are disposed near both the proximal end 116 and the distal end 114.

FIG. 5 is an alternative depiction of the system 100 with the elongated tube 104 connected to a syringe 202. Similar to FIG. 4, the distal end 114 and the proximal end 116 have tubing stripes 102 and the tactile elements 106 are disposed near both ends of the elongated tube 104. A difference between color of the elongated tube 104 and color of the fluid is perceptible so that, in dimly lit environments, a user can easily see that there is fluid in the elongated tube 104.

Tubing accessories may take on a number of forms. FIG. 6A is an exemplary depiction of a tubing accessory as a roller clamp 600, while FIG. 6B is an exemplary depiction of a tubing accessory as a side clamp 604. The tubing accessory has at least one visual or tactile indicator disposed on its surface, with the indicator corresponding to the annular feature of the elongated tube 104. Both the roller clamp 600 and side clamp 604 are used in conjunction with the elongated tube 104 to move fluid through the elongated tube 104 or expel air from the elongated tube 104. A roller clamp 600 and side clamp 604 may have stripes 602 606 on a surface of the roller clamp 600 and side clamp 604. The stripes 602 606 may be affixed to one surface of the roller clamp 600 and side clamp 604 or on multiple surfaces of the roller clamp 600 and side clamp 604. The stripes 602 606 of the roller clamp 600 and side clamp 606 correspond to the annular feature (in this instance the tubing stripes 102) of the tube 104. For instance, the roller clamp 600 has three stripes 602. This roller clamp 600 would be used with a elongated tube 104 with three tubing stripes 102 either disposed near the distal end 114 of the elongated tube 104, the proximal end 116 of the elongated tube 104, or at both the distal end

114 and proximal end 116 of the elongated tube 104. Similarly, the side clamp 604 has three stripes 606. Such a side clamp 604 would be used with an elongated tube 104 with three tubing stripes 102 either disposed near the distal end 114 of the elongated tube 104, the proximal end 116 of the elongated tube 104, or both the distal end 114 and proximal end 116 of the elongated tube 104. If there are stripes 602 606 affixed on multiple surfaces of the roller clamp 600 and side clamp 604, the number of stripes 602 606 corresponds to the number of tubing stripes 102 on an elongated tube 104. For instance, a roller clamp 600 with three stripes 602 on two surfaces is used with an elongated tube 104 with three tubing stripes 102 either disposed near the distal end 114 of the elongated tube 104, the proximal end 116 of the elongated tube 104, or both the distal end 114 and proximal end 116 of the elongated tube 104. Similarly, a side clamp 604 with three stripes 606 on two surfaces is used with an elongated tube 104 with three tubing stripes 102 either disposed near the distal end 114 of the elongated tube 104, the proximal end 116 of the elongated tube 104, or both the distal end 114 and proximal end 116 of the elongated tube 104. The indicator affixed to the roller clamp 600 and side clamp 604 (tubing accessories) corresponds to the at least one annular feature of the elongated tube 104. The indicator may take the form of stripes 602 606. For instance, if there are 3 stripes 602 606 on the roller clamp 600 and side clamp 604, there are 3 tubing stripes 102 disposed near the distal end 114 and/or proximal end 116 of the elongated tube 104.

FIG. 7 is a flowchart showing another exemplary method 700 of guiding a user in administration of a fluid to a subject. A system 702 comprising of an elongated tube with at least one annular feature disposed near the tube's distal and/or proximal end, with a reference chart and at least one tubing accessory is provided, with the elongated tube capable of accepting fluid. Step 704 introduces fluid to a container, with the container able to connect to the distal end of the elongated tube. Step 706 has a user observing the tubing stripe (example of an annular feature), with the tubing stripe disposed near either the distal or proximal end of the elongated tube. Step 708 has the user observing the roller clamp or side clamp (examples of tubing accessories); the roller or side clamp has identical stripes to the tubing stripe (e.g. if the elongated tube has 3 tubing stripes, the roller or side clamp has 3 stripes). Step 710 has the user checking the chart to ensure that the selected elongated tube is the tube that is supposed to receive the fluid in the container; it allows a user to check that the tubing information on the chart matches the tubing stripe on the elongated tube. With step 712, the user connects the distal end of the elongated tube to the container with the fluid, with step 714 being the fluid being introduced into the elongated tube via the elongated tube's distal end. Step 716 is administering the fluid to the subject via the proximal end of the tube.

FIG. 8 is a flowchart showing another exemplary method 800 of guiding a user in administration of fluid to a subject. With the method 800, the system 802 comprises a tube with at least one tactile element disposed near either the tube's distal or proximal end, a chart with tubing information, and at least one tubing accessory. Step 804 has fluid introduced to a container. Step 806 has a user physically touch or feel the tactile elements on the tube to ensure the correct tube is selected. Step 808 has the user observe the roller or side clamp (example of tubing accessories). Step 810 has a user check the chart to ensure the tubing information on the chart matches the tube. Step 812 has the user attach the distal end of the tube to the container holding the fluid, with step 814 being the fluid being introduced to the tube. Step 816 is the fluid being administered to the subject via the tube's proximal end.

FIG. 9 is a flowchart showing yet another exemplary method 900 for guiding a user in administration of a fluid to a subject. Step 902 provides a system that comprises a tube, at least one annular feature at the distal or proximal end of the tube, at least one tactile element at the distal or proximal end of the tube, a chart with tubing information, and at least one tubing accessory. Step 904 has a user introduce fluid to a container, with the fluid ultimately entering the distal end of the tube. Step 906 has the user observe the tubing stripe (example of an annular feature) and physically touch the tactile element to ensure the correct tube receives the correct fluid. Step 908 has the user observe the roller clamp or side clamp (examples of tubing accessories); the roller or side clamp has stripes that mirror those of the tubing stripes on the elongated tube (same color and number). This is to ensure the intended roller or side clamp is used with the intended tube. Step 910 has the user check the chart to make sure the tubing information on the chart matches the stripes and/or tactile elements on the tube. Step 912 has the user connect the distal end of the tube to the container holding the fluid. Those of skill in the art recognize that there is a myriad of ways to make this connection. Step 914 has the user introduce the fluid to the tube, with the proximal end of the tube connected to the subject to receive the fluid. Step 916 is the fluid being administered to the subject via the proximal end of the tube. Care is taken to ensure that there are no bubbles in the tube, as bubbles entering the subject can have deleterious effects. If there are bubbles, they are removed from the tube by exposing the distal end of the tube to the atmosphere and using the roller or side clamps to remove the bubbles.

FIGS. 10A-C are exemplary depictions of an elongated tube 104 with multiple tubing stripes 102 and tactile elements 106. The tactile elements 106 may be in direct contact with the tubing stripes 102. The tactile elements 106 may also be in close proximity to the tubing stripes 102 without being in direct contact. FIG. 10A with three tubing stripes 102 and three tactile elements 106 disposed near the distal end 114 and proximal end 116 of the tube. FIG. 10B with one tubing stripe 102 and one tactile element 106 disposed near the distal end 114 and proximal end 116 of the tube, and FIG. 10C with two tubing stripes 102 and two tactile elements 106 disposed near the distal end 114 and proximal end 116 of the tube, will be used with different fluids. In any depiction, the tubing stripes 102 and tactile elements 106 may be disposed near the distal end 114 of the elongated tube 104, the proximal end 116 of the elongated tube 104, or both the distal end 114 and the proximal end 116 of the elongated tube 104.

FIGS. 11A-B are exemplary depictions of an elongated tube 104 with tubing stripes 102 and tactile elements 106 of various thicknesses. FIG. 11B clearly shows tubing stripes 102 that are thicker than the tubing stripes 102 in FIG. 11A. The thickness of the tubing stripe 102 may vary, ranging from around 0.01 inches to around 1 inch. It is inadvisable to use elongated tubes 104 with varying thicknesses together. Elongated tubes 104 with 0.1 inch thick tubing stripes 102 should not be mixed with elongated tubes 104 with 0.25 inch tubing stripes 102. Especially in dimly lit environments, it would be difficult to differentiate between the 0.1 inch-thick tubing stripes 102 and the 0.25 inch-thick tubing stripes 102. To minimize error, elongated tubes 104 with 0.1 inch thick tubing stripes 102 are used together, and elongated tubes 104 with 0.25 inch thick tubing stripes 102 are used together. The tubing stripes 102 and tactile elements 106 may be disposed near the distal end 114 of the elongated tube 104, the proximal end 116 of the elongated tube 104, or both the distal end 114 and the proximal end 116 of the elongated tube 104.

FIGS. 12A-B are exemplary depictions of an elongated tube 104 with tubing stripes 102 and tactile elements 106 of various spacing. FIG. 12B clearly shows tubing stripes 102 that are spaced more closely than the tubing stripes 102 in FIG. 12A. The spacing of the tubing stripe 102 may vary, ranging from around 0.01 inches to around 1 inch. It is inadvisable to use elongated tubes 104 with varying spacing together. Elongated tubes 104 with 0.2 inch spaced tubing stripes 102 should not be mixed with elongated tubes 104 with 0.3 inch spaced tubing stripes 102. Especially in dimly lit environments, it would be difficult to differentiate between the 0.2 inch-spaced tubing stripes 102 and the 0.3 inch spaced tubing stripes 102. To minimize error, elongated tubes 104 with 0.2 inch spaced tubing stripes 102 are used together, and elongated tubes 104 with 0.3 inch spaced tubing stripes 102 are used together. The tubing stripes 102 and tactile elements 106 may be disposed near the distal end 114 of the elongated tube 104, the proximal end 116 of the elongated tube 104, or both the distal end 114 and the proximal end 116 of the elongated tube 104.

FIGS. 13A-B show exemplary depictions of a visual-tactile combination indicator 1302 encircling an elongated tube 104. FIG. 13A has two visual-tactile combination indicators 1302 disposed near the distal end 114 and proximal end 116 of the elongated tube 104, while FIG. 13B has one visual-tactile combination indicator 1302 disposed near the distal end 114 and proximal end 116 of the elongated tube 104. The thickness and spacing of the visual-tactile combination indicator 1302 vary, ranging from about 0.01 inches to about 1 inch. It is inadvisable to use visual-tactile combination indicators 1302 of differing thicknesses and spacing together, as it would be difficult to differentiate between the different types of thicknesses and spacing. The visual-tactile combination indicator 1302 may be disposed near the distal end 114 of the elongated tube 104, the proximal end 116 of the elongated tube 104, or both the distal end 114 and the proximal end 116 of the elongated tube 104.

EXAMPLES

Aspects of the present teachings may be further understood in light of the following examples, which should not be construed as limiting the scope of the present teachings in any way.

Example 1—Use of the System in an Emergency

During the transport of a subject, the subject is packaged in a blanket, and secured with belts for safety. It is incredibly difficult to administer fluid once the subject is ready for transport, unless the port or entry point for delivering the fluid is visible. Should a port be needed in an emergency during transport, any member of the transport team can recognize tubing by feeling the number of bumps in a row at one end, and calling the number out to another crew member. In a helicopter transport environment, the subject's entry port is in the subject's lower extremity, which is in close proximity to the pilot. The pilot can aid the transport team by feeling the number of bumps in a row at the end of the tubing closest to the pilot. In this instance, as in others, the tubing stripes and bumps being at the ends of the tube make it easy for transport staff and the pilot to see bubbles in the tube. Tubing stripes existing at other positions on the tube, such as down the length of the tube, obscures the bubbles, making it difficult to see bubbles in the tube. Bubbles in the tube prevent the optimal amount of fluid being administered to the subject. In addition, tubing stripes down the length of the tube obscures the color of the fluid. Being able to see the color of the fluid acts as a secondary measure to ensure that correct fluid is administered to the subject. In addition, having stripes down the length of the tube makes it difficult to count stripes. Even though the tactile elements are typically what is counted to ensure the correct fluid is being directed to the correct tube, counting stripes may act as a secondary measure to ensure the correct fluid is entering the correct tube. Also, stripes down the length of the tube may cause color fatigue. Having stripes concentrated at the ends of the tube may it less likely that one handling the tube would mistake it for another tube.

Example 2—Stripe Color and Tactile Element Configuration

There are multiple colors for the stripes, with corresponding number of tactile elements and tubing entry points. Each color stripe and tactile element configuration corresponds to a different fluid and entry point, as seen for example in Table 1. Based on the stripe color and number of tactile elements, a different fluid type is delivered to a subject at a different entry point. It must be noted that Table 1 is an example of the stripe color and tactile element combinations. Many different stripe color and tactile element combinations are possible. The user of the system may designate which color stripe and tactile element are assigned to which fluid and entry point.

maintain blood pressure, and a line where intermittent medications can be administered. Throughout the case, the surgeon inserts cardiac catheters with multiple lumens into the atria and pulmonary artery. These catheters require heparinized saline running at a low continuous rate in order to keep the line patent. The case ends and the patient is transferred to an intensive care unit bed. There the patient is immediately connected to the monitor while the surgical team provides a report on the events in the operating room. The patient needs at minimum a chest x-ray and a 12-lead ECG upon admission. Multiple labs must be drawn from the arterial line for analysis, and the patient needs sedation. The Registered Nurse (RN) draws up a dose of fentanyl and administers it through an available port. But this patient and all the lines are new to the RN and she must search for a port that will not interfere with any medication that cannot be interrupted. The patient calms after the sedation, but then requires titration of his blood pressure medication. The nurse pauses in her assessment of her patient, catheters, and lines to attend to the blood pressure. Throughout this whole process, there are multiple interruptions that delay the ability of the bedside nurse to assess that all the medications are being administered correctly. To keep track of the various medications that need to go to the patient, the nurse ensures that the appropriate tube receives the correct medication. A tube for continuous hydration may be a tube with 2 orange stripes and a row of 2 tactile elements. A tube for sedation may be a tube with 3 red stripes and a row of 3 tactile elements. A tube for maintaining blood pressure may be a tube with 2 blue stripes and a row of 2 tactile elements

OTHER EMBODIMENTS

The detailed description set-forth above is provided to aid those skilled in the art in practicing the present invention.

TABLE 1

Configuration of tubing stripes, tactile elements, and entry points

| Stripe color | Number of tactile elements in a row | Material | Entry point |
|---|---|---|---|
| Red | 1 | Low flow carrier fluid | Arterial line |
| Orange | 1 | Low flow carrier fluid | Peripheral intravenous |
| | 2 | Continuous intravenous fluid or Total parenteral nutrition | Peripheral intravenous |
| | 3 | Sedation medication | Peripheral intravenous |
| | 4 | High-risk infusions (inotropes, insulin, heparin) | Peripheral intravenous |
| | 5 | Chemotherapy medication | Peripheral intravenous |
| Green | 1 | Low flow carrier fluid | Peripheral intravenous |
| | 2 | Continuous intravenous fluid or Total parenteral nutrition | Peripheral intravenous |
| | 3 | Sedation medication | Peripheral intravenous |
| | 4 | High-risk infusions (inotropes, insulin, heparin) | Peripheral intravenous |
| | 5 | Chemotherapy medication | Peripheral intravenous |
| Blue | 1 | Low flow carrier fluid | Central venous line |
| | 2 | Continuous intravenous fluid or Total parenteral nutrition | Central venous line |
| | 3 | Sedation medication | Central venous line |
| | 4 | High-risk infusions (inotropes, insulin, heparin) | Central venous line |
| | 5 | Chemotherapy medication | Central venous line |
| Purple | 1 | Low flow carrier fluid | Peripherally Inserted Central Catheter |
| | 2 | Continuous intravenous fluid or Total parenteral nutrition | Peripherally Inserted Central Catheter |
| | 3 | Sedation medication | Peripherally Inserted Central Catheter |
| | 4 | High-risk infusions (inotropes, insulin, heparin) | Peripherally Inserted Central Catheter |
| | 5 | Chemotherapy medication | Peripherally Inserted Central Catheter |

Example 3—Using the Correct Tubes to Administer the Correct Medications to the Correct Locations A patient is admitted to the operating room for cardiac surgery and the anesthesiologist inserts an arterial line and a central line. The patient has continuous intravenous fluids for hydration, as well as sedation medication, medication to However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

What is claimed:

1. A coding system for guiding a user in administration of a fluid to a subject, comprising:
   a plurality of elongated tubes, each elongated tube formed from a tubing material and having a distal end and a proximal end;
   at least one annular feature disposed near each of the proximal end and the distal end of each elongated tube, wherein the at least one annular feature is one or a combination of visually distinguishable and tactilely distinguishable from the tubing material, wherein the at least one annular feature comprises a plurality of annular stripes imprinted on or embedded in the tubing material and separated by spacings, and wherein the at least one annular feature is different for each elongated tube of the plurality of elongated tubes, and wherein the plurality of annular stripes at the proximal end and the distal end of each elongated tube comprises a matching combination of stripes and spacings; and
   a reference chart that identifies to the user the at least one annular feature as associated with one or more of a fluid source, a connector and a tubing accessory to which the tube is to be connected.

2. The system of claim 1, wherein the tubing accessory is a clamp, wherein the clamp has at least one visual or tactile indicator disposed on a surface thereof corresponding to the at least one annular feature.

3. The system of claim 1, wherein the plurality of annular stripes comprise one or more of visually distinguishable colors, hues, patterns, thicknesses, and spacings.

4. The system of claim 1, wherein each stripe of the plurality of annular stripes comprises one or a combination of tactile elements selected from a raised annular rib, an array of bumps, a ring of bumps, an annular groove, an array of dimples, and a ring of dimples.

5. The system of claim 4, wherein the one or a combination of tactile elements comprise one or more of visually distinguishable colors, patterns, thicknesses, and spacings.

6. The system of claim 1, wherein the at least one annular feature comprises a plurality of annular features comprising a combination of stripes and tactile elements.

7. A method of guiding a user in administration of a fluid to a subject, comprising:

providing a coding system for guiding the user in administration of the fluid to the subject, the system comprising:
   a plurality of elongated tubes, each elongated tube formed from a tubing material and having a distal end and a proximal end;
   at least one annular feature disposed near each of the proximal end and the distal end of each elongated tube, wherein the at least one annular feature is one or a combination of visually distinguishable and tactilely distinguishable from the tubing material, wherein the at least one annular feature comprises a plurality of stripes imprinted on or embedded in the tubing material and separated by spacings, and wherein the at least one annular feature is different for each elongated tube of the plurality of elongated tubes, and wherein the plurality of annular stripes at the proximal end and the distal end of each elongated tube comprises a matching combination of stripes and spacings; and
   a reference chart that identifies to the user the at least one annular feature as associated with one or more of a fluid source, a connector and a tubing accessory to which the tube is to be connected;
introducing the fluid to a container;
observing the at least one annular feature so that the fluid corresponds to the at least one annular feature;
connecting the distal end of an associated elongated tube to the container and the proximal end of the associated elongated tube to the subject;
introducing the fluid to the associated elongated tube; and
administering the fluid to the subject.

8. The method of claim 7, wherein the fluid is documented on the reference chart.

9. The method of claim 7, wherein the plurality of annular stripes comprise one or more of visually distinguishable colors, hues, patterns, thicknesses, and spacings.

10. The method of claim 7, wherein each stripe of the plurality of annular stripes comprises one or a combination of tactile elements selected from a raised annular rib, an array of bumps, a ring of bumps, an annular groove, an array of dimples, and a ring of dimples.

11. The method of claim 10, wherein the one or a combination of tactile elements comprise one or more of visually distinguishable colors, patterns, thicknesses, and spacings.

12. The method of claim 7, wherein the at least one annular feature comprises a plurality of annular features comprising a combination of stripes and tactile elements.

* * * * *